(12) United States Patent
Chang et al.

(10) Patent No.: US 7,410,063 B1
(45) Date of Patent: Aug. 12, 2008

(54) METHOD AND SYSTEM FOR SORTING PARTICLES SAMPLED FROM AIR

(75) Inventors: Richard K. Chang, Hamdin, CT (US); Yongle Pan, Cheshire, CT (US); Steven Clyde Hill, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 49 days.

(21) Appl. No.: 10/872,414

(22) Filed: Jun. 22, 2004

Related U.S. Application Data (63) Continuation-in-part of application No. 10/360,767, filed on Jun. 19, 2002, now Pat. No. 6,947,134, which is a continuation-in-part of application No. 09/579,707, filed on May 25, 2000, now Pat. No. 6,532,067.

(60) Provisional application No. 60/147,794, filed on Aug. 9, 1999.

(51) Int. Cl.
*B07C 5/00* (2006.01)

(52) U.S. Cl. .................. 209/44.2; 209/579; 209/587; 209/644

(58) Field of Classification Search .............. 209/44.2, 209/143, 576, 579, 587, 644, 939
See application file for complete search history.

(56) References Cited

U.S. PATENT DOCUMENTS 3,380,584 A * 4/1968 Fulwyler .................. 209/3
3,976,862 A * 8/1976 Curbelo .................... 702/46

(Continued)

OTHER PUBLICATIONS

Fluorescence Spectra of Atmospheric Aerosol at Adelphi, Maryland, USA: Measurement and Classification of Single Particles Containing Organic Carbon, Atmospheric Environment, 38, 1657-1672 (2004), Pinnick, Ronald G.; Hill, Steven C.; Pan, Yong-le; Chang, Richard K.

(Continued)

*Primary Examiner*—Joseph C Rodriguez
(74) *Attorney, Agent, or Firm*—William V. Adams; William W. Randolph (57) ABSTRACT

Methods and systems for sorting particles entrained in a gaseous stream are disclosed. A representative system, among others, includes a particle scanner, a sorter, which is in pneumatic communication with the particle scanner, and a controller, which is in electrical communication with the particle scanner and sorter. The particle scanner is adapted to receive a gaseous stream and measure a characteristic of a particle entrained in the gaseous stream. The controller is adapted to classify the scanned particle according to the measured characteristic of the particle. The sorter includes an electrically controlled valve. Responsive to the particle being classified as belonging to a first category, the controller signals the valve to deflect the trajectory of the particle.

A representative method, among others, for sorting particles entrained in a gaseous stream can be broadly summarized by the following steps: receiving particles in a gaseous stream; classifying a particle from the received stream of particles according to a property of the particle, wherein the particle is classified as belong to one category of a plurality of categories, and wherein the received particle has an initial trajectory; and responsive to the particle being classified as belonging to a first category of the plurality of categories, altering the trajectory of the particle.

12 Claims, 4 Drawing Sheets

U.S. PATENT DOCUMENTS

| | | | |
|---|---|---|---|
| 4,184,766 A * | 1/1980 | Hogg | 356/72 |
| 4,606,232 A | 8/1986 | Prodl | |
| 4,609,108 A * | 9/1986 | Hristozov et al. | 209/581 |
| 4,639,311 A | 1/1987 | Prodi | |
| 4,793,832 A | 12/1988 | Veltman et al. | |
| 4,848,590 A * | 7/1989 | Kelly | 209/564 |
| 5,413,222 A | 5/1995 | Holder | 298/567 |
| 5,628,411 A * | 5/1997 | Mills et al. | 209/644 |
| 5,779,058 A * | 7/1998 | Satake et al. | 209/581 |
| 5,967,332 A | 10/1999 | Willeke | |
| 6,078,018 A | 6/2000 | Davis et al. | |
| 6,260,712 B1 * | 7/2001 | Flottmann et al. | 209/639 |
| 6,497,324 B1 * | 12/2002 | Doak et al. | 209/522 |
| 6,532,067 B1 | 3/2003 | Chang et al. | |
| 6,646,218 B1 * | 11/2003 | Campbell et al. | 209/582 |
| 2002/0030707 A1 * | 3/2002 | Arnold et al. | 347/9 |
| 2004/0125371 A1 | 7/2004 | Chang | |
| 2005/0173313 A1 * | 8/2005 | Tyvoll et al. | 209/644 |

OTHER PUBLICATIONS

Single-Particle Fluorescence Spectrometer for Ambient Aerosols, Aerosol Science and Technology 327:627-638 (2003), Pan, Yong-le; Hartings, Justin; Pinnick, Ronald G.; Hill, Steven C.; Halverson, Justin; Chang, Richard K.

Patent Application entitled "Systems and Methods for Sorting Aerosols", by Chang, Richard, document date Jan. 28, 2004, assigned U.S. Appl. No. 10/766,294.

* cited by examiner

METHOD AND SYSTEM FOR SORTING PARTICLES SAMPLED FROM AIR

CROSS-REFERENCE TO RELATED APPLICATION

This application is a Continuation-In-Part of U.S. utility patent application entitled "Method and Instrumentation for Measuring Fluorescence Spectra of Individual Airborne Particles Sampled From Ambient Air" filed on Jun. 19, 2002, and accorded Ser. No. 10/360,767, now U.S. Pat. No. 6,947,134 which is a Continuation-In-Part of U.S. utility application accorded Ser. No. 09/579,707 filed May 25, 2000, which issued as U.S. Pat. No. 6,532,067 on Mar. 11, 2003, which in turn claims priority to U.S. provisional application accorded Ser. No. 60/147,794 filed Aug. 9, 1999, all of which are entirely incorporated herein by reference.

GOVERNMENT INTEREST

The invention described herein may be manufactured and used by or for the United States Government for governmental purposes without the payment of any royalties thereon.

BACKGROUND

1. Technical Field

The present invention is generally related to the sorting of particles.

2. Description of the Related Art

The collection and monitoring of particles separated from a gas is needed in many diverse situations. Some of these situations include defense against biological warfare agents in battlefield and other military applications; and protecting the general public against: airborne pathogenic agents released by terrorist groups; genetically modified material used in biotechnology applications; infectious organisms contaminating air in hospitals, research labs, public buildings, and confined spaces such as subway systems; and pollutant aerosols that damage the respiratory system. The collection and measurement of infectious organisms are of interest to a wide community of public health officials because they can cause infectious diseases or chemical damage to the respiratory system. These particles are also of concern to the Department of Defense (DOD) because of their possible use in biological warfare and terrorism.

Air quality monitoring is also an important public health need. As the world's population rises and world travel becomes increasingly easy, the degree and pace at which communicable diseases can spread has resulted in significant concerns regarding potential epidemics from airborne disease transmission. Recirculation of air in buildings and other enclosed spaces such as subways and airplanes has lead to a potentially significant public health issues. Identification and control of infectious disease organisms in hospitals represents another major need. The Environmental Protection Agency cites indoor air pollution causing "sick building syndrome" as a major environmental problem in the United States.

Threats from microorganisms in the air as a result of natural phenomena or human-induced activities such as the examples discussed above cannot be adequately monitored and evaluated with current technology. Early warning, hazard recognition, personal protective equipment, exposure evaluation, and environmental monitoring are needed to prevent and reduce impacts from airborne infectious or genetically modified material. Near real-time monitoring is necessary to avoid exposure and to initiate early treatment to arrest disease progression.

SUMMARY

Systems and methods for sorting particles in a gaseous stream are provided. Briefly described, one embodiment of an apparatus includes a scanner, a sorter, which is in pneumatic communication with the scanner, and a controller, which is in electrical communication with the scanner and sorter. The scanner is adapted to receive a gaseous stream and measure a characteristic of a particle entrained in the gaseous stream. The controller is adapted to classify the scanned particle according to the measured characteristic of the particle. The sorter includes an electrically controlled valve. Responsive to the particle being classified as belonging to a first category, the controller signals the valve to deflect the trajectory of the particle.

An embodiment of a method can be broadly summarized by the following steps: receiving particles in a gaseous stream; classifying a particle from the received stream of particles according to a property of the particle, wherein the particle is classified as belong to one category of a plurality of categories, and wherein the received particle has an initial trajectory; and responsive to the particle being classified as belonging to a first category of the plurality of categories, altering the trajectory of the particle.

Other systems, methods, features, and/or advantages will be or may become apparent to one with skill in the art upon examination of the following drawings and detailed description. It is intended that all such additional systems, methods, features, and/or advantages be included within the description and be protected by the accompanying claims.

BRIEF DESCRIPTION OF THE DRAWINGS

The components in the drawings are not necessarily to scale. Moreover, in the drawings, like reference numerals designate corresponding parts throughout the several views.

DETAILED DESCRIPTION

Figure 1:
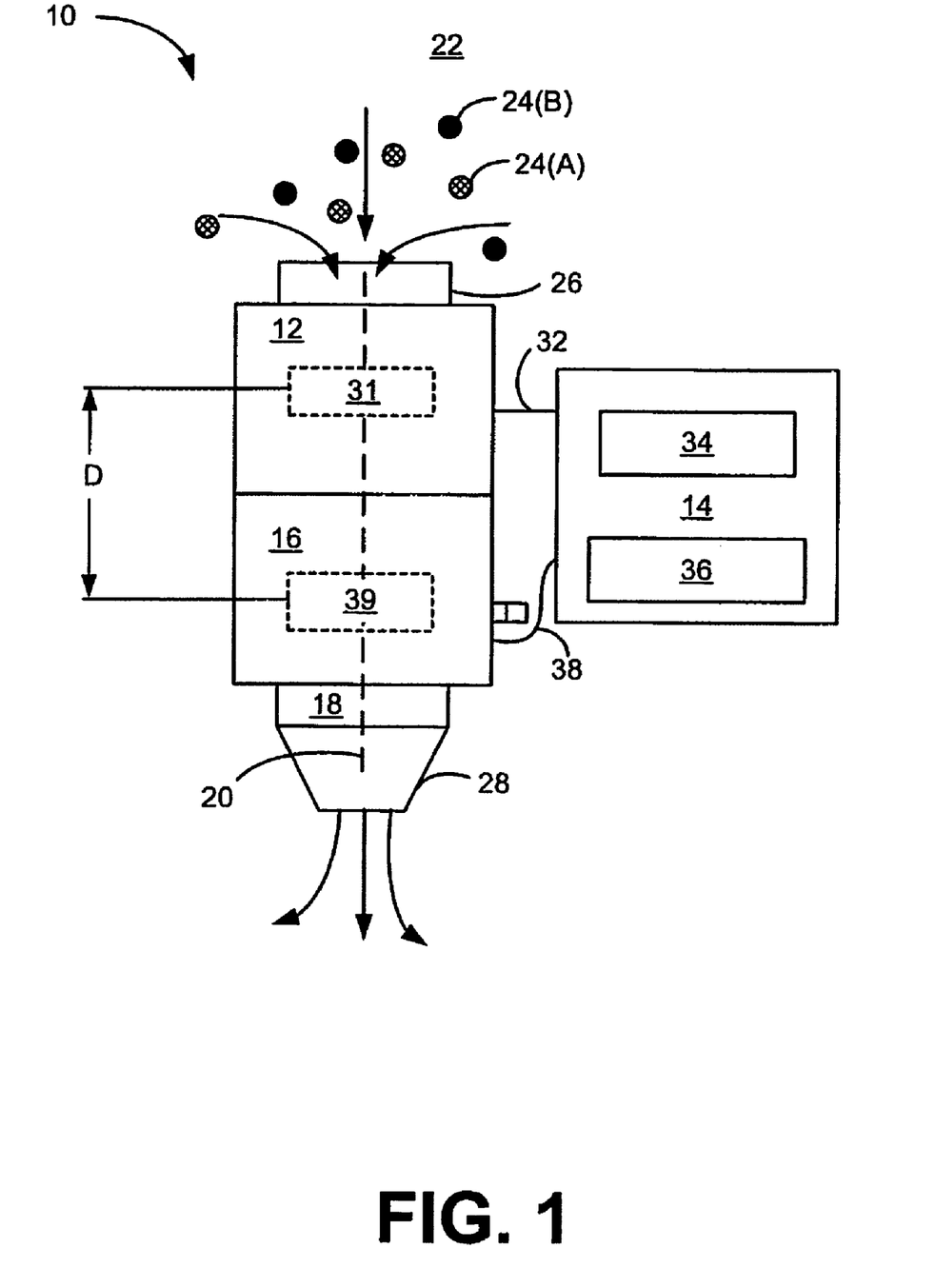
FIG. 1 is a block diagram of an embodiment of an aerosol particle sorter system (APSS).

Referring to FIG. 1, an embodiment of a aerosol particle sorter system (APSS) 10 includes components such as a particle scanner 12, a controller 14, a particle sorter 16 and a pump 18, which are approximately longitudinally aligned and which approximately define a longitudinal axis 20. The APSS 10 is immersed in a gas 22, such as the atmosphere, having particles 24 therein. The pump 18 draws gas and particles into the APSS 10 through an induction port 26 and exhausts at least the gas out of an eduction port 28. Generally, the particles 24 include many types of particles, which may be classified into predetermined categories. For example, all of the particles of type 24(A) can belong to category 1; all of the particles of type 24(B) belong to category 2 and so on.

Gas 22 and particles 24 are drawn from the induction port 26 into the particle scanner 12. The particle scanner 12 scans the particles 24 as the particles flow through the particle scanner 12. From the particle scanner 12, the gas 22 and particles 24 flow into the particle sorter. The pump 18 draws the gas through the particle sorter 16 and exhausts at least the gas 22 through the eduction port 28.

As particles 24 are drawn through the particle scanner 12, the particles pass through region 31, which is known as the scan zone. When a particle in the scan zone 31, the particle scanner 12 measures physical and/or optical properties or characteristics of the scanned particles 24 while the particles are in a scan zone 31. The measured quantities are provided to the controller 14 via an electrical connection 32.

The controller 14 includes a processor 34 and a particle characteristic database 36. The particle characteristic database 36 includes known physical and/or optical properties of various particles. The processor 34 uses the measured quantities reported by the particle scanner 12 to determine whether a scanned particle belongs to a category of particles and whether the category of particles is one of interest. Generally, particles of interest are sorter from uninteresting particles, and the other particles exit the APSS 10 via the eduction portion 28.

Whether or not a particle is of interest or not depends upon the category of the particle, and categories are established by the operator of the APSS 10. Having identified a particle of interest, the controller 14 sends a trigger signal to the particle sorter 16, via an electrical connection 38, which prompts the particle sorter 16 to sort particles of interest from other particles when the particles of interest are in a target zone 39.

Generally, the APSS 10 is used to sort airborne particles and, in that case, the mean velocity (v) of the particles through the APSS 10 is governed by the pump 18. The distance (D) between the scan zone 31 and the target zone 39 is fixed and known. Consequently, the time (t) for a particle of interest to traverse the distance D is simply D divided by v(t=D/v). The controller 14 triggers the particle sorter 16 at the appropriate time such that the particle of interest is in the target zone. In some embodiments, the controller 14 calculates the delay time between when a particle is in the scan zone 31 and when it is in the target zone 39. In some alternative embodiments, the operator of the APSS 10 provides the delay time to the APSS 10.

In some embodiments, the APSS 10 is used to sort particles when there is no gas flow through the instrument, i.e., particles that are not carried by an airflow through the instrument, but instead fall through the instrument because of gravitational acceleration. In this embodiment, the APSS 10 is aligned generally vertically and the particle scanner 12 detects a particle at two or more different vertical locations. The controller 14 then determines the velocity of the particle. In some embodiments, the controller 14 can also determine the acceleration of the particle. Generally, the acceleration is not necessary because the particles are normally falling at their terminal velocity. The controller 14 is adapted to determine the delay time between when a particle is scanned and when it is in the target zone 39 so that particles of interest can be sorted.

Generally, the APSS 10 is used to sort airborne particles whose drift rate through the APSS 10 is approximately that of the gas. In some embodiments, the pump 18 induces a drift rate of approximately 10 meters per second through the APSS 10. The controller 14 knows the drift rate (10 m/sec.) and the longitudinal position of where particles are scanned and the longitudinal position of where particles are sorted. Thus, for the case of particles having constant velocity, the trigger signal for sorting a given particle is a known constant delay from the time at which the particle is scanned.

Figure 2:
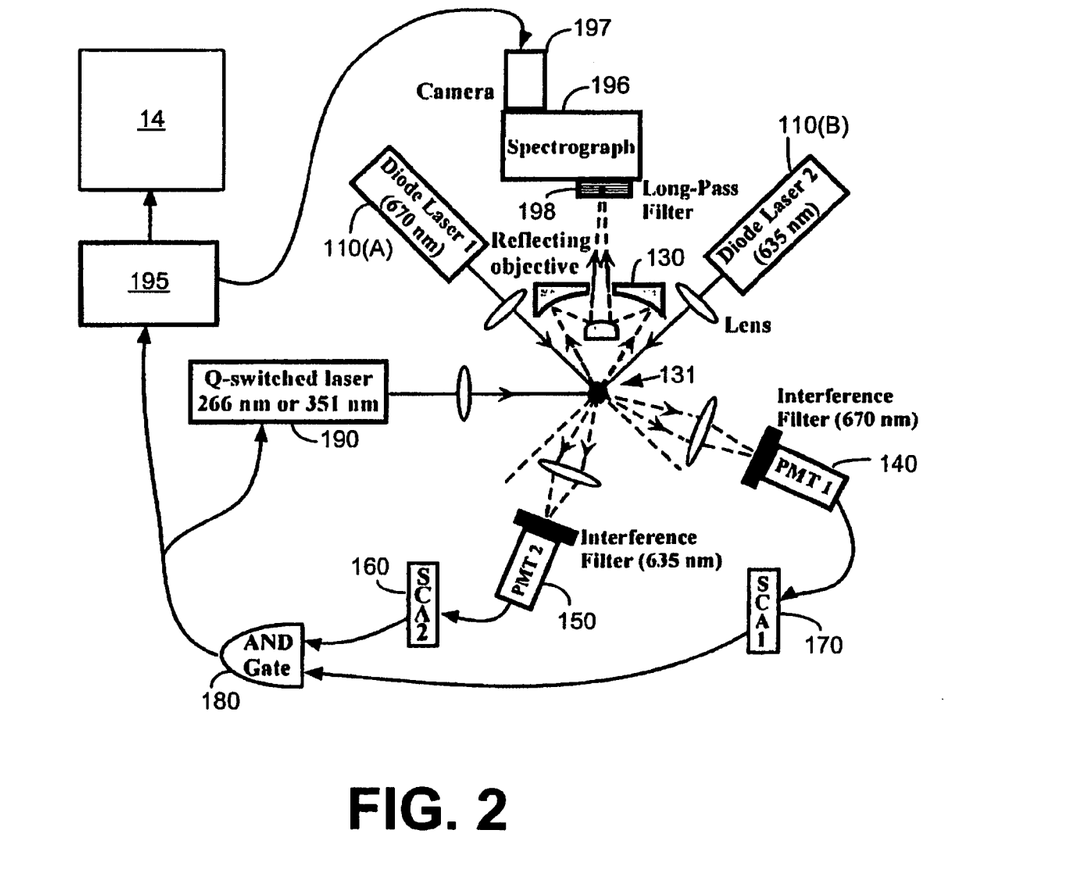
FIG. 2 is a block diagram of an embodiment of a particle scanner.

Referring to FIG. 2, which illustrates components of the particle scanner 12 as seen from above, particles entrained within a stream of air are drawn into the particle scanner 12 and are directed downward toward the scan zone 31. The scan zone 31 is defined by two nearly orthogonal, different-wavelength laser trigger beams (Lasers 110(A) and 110(B)), which are aimed and focused precisely to define an approximate 15-μm diameter focal volume position just upstream (about 50 micron) of a first focal plane of reflecting objective 130. In some embodiments, the lasers 110(A) and 110(B) are diode lasers 1 and 2, respectively, which respectively emit light at 670 and 635 nm.

As a particle 24 passes through the intersection of trigger beams from lasers 110(A) and 110(B) (defined as the trigger volume), light is scattered from the particle 24 and is detected by photomultipliers (PMTs) 140 and 150. PMT 140 is equipped with a narrowband interference filter such that it only detects light scattered from the trigger beam from laser 110(A).

Likewise, PMT 150 is equipped with a narrowband interference filter so that it may only detect scattered light from the trigger beam from diode laser 110(B). The intensity of the scattered light may be approximately proportional to the size of the particle. To avoid detection of particles outside the size range of interest, the output signals from PMTs 140 and 150 are processed by a pair of single channel analyzers (SCA) 160 and 170 which operate as discriminators in a window mode.

The PMT output pulses must exceed a preset lower voltage level and be less than a preset higher voltage level (as set in the window mode) before the SCA may provide an output pulse. Thus, fluorescence spectra are measured only for particles falling within a preset size interval.

The two SCA outputs are fed into a logic AND gate 180, which produces an output pulse only when the SCA output signals overlap. The output of AND gate 180 triggers a probe laser 190 to fire and also turns on a camera controller 195, which activates the a camera 197 to record only when the probe laser 190 fires. Thus, particles not flowing through trigger volume 131, which would not be illuminated by the central portion of the beam from the probe laser 190, and which are not in the focal region of reflecting objective 130, are ignored. In some embodiments, the probe laser 190 is a Q-switched UV laser.

The system is completed by spectrograph 196 with long pass filter 198, which disperses the fluorescence to camera 197 and camera controller 195. The output of camera controller 195 is fed to the controller 14 where data may be displayed, stored and analyzed. In particular, pattern recognition algorithms are employed by the controller 14 to detect and classify the particles 24.

Various modifications and alternatives are possible. For example, in an alternative embodiment, leakage of scattering from trigger beams from lasers 110(A) and 110(B) may be eliminated by signaling the lasers to turn off using the same signal from the logic circuit as is used to trigger the probe laser 190. Probe laser 190 is preferably a tightly focused pulsed UV laser triggerable on demand and of sufficiently high intensity or fluency to excite fluorescence in microparticles.

In a preferred embodiment, probe laser 190 is a Q-switched UV laser, either 266 nm, 4th harmonic of a Nd:YAG laser, 30- or 70-ns pulse duration, 0.1 to 0.2 mJ per pulse (Spectra Physics models X-30 or Y-70), or 351 nm, 3rd harmonic of a Nd:YLF laser, 120 ns pulse duration, 1.65 mJ per pulse (Quantronix). The Q-switched laser was set to fire within approximately 3 microseconds of the trigger pulse (from the AND circuit), during which time the particle traveled (at a speed of about 10 m/s) about 30 micrometers. Various other probe lasers may be employed, depending on the type of particle and fluorescence to be detected.

The vertical displacement between the location where the particle is detected (trigger volume) and the location where the particle is probed (detection volume) can be compensated for by a small vertical displacement of the focal volume of trigger beams from lasers 110(A) and 110(B) and the beam from probe laser 190, which is focused at a focal plane of the reflecting objective.

Alternatively, the displacement of these two volumes may be compensated for by a variable electronic delay, with the delay based on the speed at which particles are introduced into the focal volume.

In some embodiments, multiple-wavelength excitation (e.g., one wavelength within the absorption band for tryptophan, and a longer wavelength for other biological molecules) may be used to better identify biological particles.

Reflecting objective 130 preferably has a large numerical aperture that can collect fluorescence from the emitting particle over a large solid angle, and focus it onto the slit of a spectrograph without chromatic aberration. In a preferred embodiment, reflective objective 130 (a so-called Schwartzchild reflecting objective) is manufactured by the Ealing Company and has numerical aperture 0.5.

Alternatively, the sensitivity of the particle scanner 12 may be increased by adding a spherical reflector on the side opposite the Schwartzchild objective, or by replacing the Schwartzchild reflective objective 130 with a parabolic or ellipsoidal reflector. With this modification, particles would be excited to fluoresce when they traverse the focal point of the reflector. The parabolic reflector would collect the fluorescence, which would be focused onto the slit of spectrograph 196 as with the Schwartzchild reflecting objective. The ellipsoidal reflector may collect the fluorescence and focus it onto the slit of the spectrograph 196 positioned at the second focal point of the mirror.

In another embodiment, the camera 197 is manufactured by Princeton Instruments. Camera 197 is placed at the exit port of the spectrograph 196 (an Acton model SP-150 with 300 groove/mm grating blazed at 500 nm, numerical aperture 0.125, input slit width 1 mm). The image intensifier of camera 197 acts as a fast shutter, opening when the targeted particle is illuminated by the UV laser. A long pass filter 198 is placed in front of spectrograph 196 to block elastically-scattered light and to pass the fluorescence.

In another embodiment, the camera 197 is a multiple-channel photomultiplier tube (PMT), and the camera controller 195 is manufactured by Vtech. However, in alternative embodiments, a multiplexer can also be used. A multiple-channel PMT provides the advantages of comparable sensitivity, compactness, lighter weight, and lower cost, as compared to other controllers such as an intensified charge coupled device controller. A 32 channel system provides sufficient spectral resolution to classify bioaerosol particles and provides for rapid sampling of aerosol particles and portability.

Further details of a particle scanner 12 can be found in U.S. patent application Ser. No. 10/360,767, which is hereby incorporated by reference. In addition further details regarding fluorescence of ambient aerosols including biological particles can be found in the following publications, which are hereby incorporated by reference: "Fluorescence Spectra of Atmospheric Aerosol at Adelphi, Md., USA: Measurement and Classification of Single Particles Containing Organic Carbon," Atmospheric Environment, 38, 1657-1672 (2004), Pinnick, Ronald G.; Hill, Steven C.; Pan, Young-le; Chang, Richard K.; and "Single-Particle Fluorescence Spectrometer for Ambient Aerosols," Aerosol Science and Technology 37:627-638 (2003), Pan, Yong-le; Hartings, Justin; Pinnick, Ronald G.; Hill, Steven, C.; Halverson, Justin; Chang, Richard K.

Figure 3:
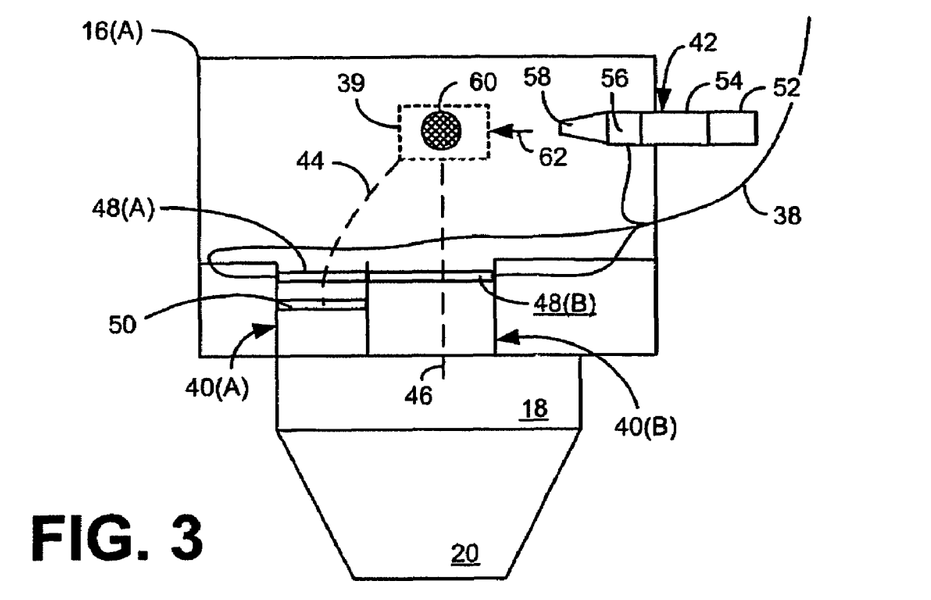
FIG. 3 is a block diagram of an embodiment of a particle sorter.

FIG. 3 illustrates a first embodiment of the particle sorter 16. In this embodiment, the particle sorter 16(A) includes particle receptors 40(A) and 40(B), and a particle deflector 42. The particle receptors 40 are in pneumatic communication with the pump 18. The dashed lines 44 and 46 represent two different trajectories, trajectory I and trajectory II, respectively, for particles 24. Particles classified as belonging to category 1 travel generally along trajectory I and particles classified as belonging to category 2 travel generally along the trajectory II.

In the embodiment illustrated in FIG. 3, particles 24(A) are in category 1 and are the type that are of interest. It is desired that these particles be separated from other particles in the gas 22. The particle receptor 40(A) includes a valve 48(A) and a filter 50. The valve 48(A) generally remains closed until it is triggered by the controller 14 to open. The filter 50 is adapted to filter particles 24(A) out of the gas.

The particle receptor 40(B) also includes a valve 48(B). The valve 48(B) remains generally open unless it is triggered by the controller 14 to close. Generally, one of the valves 48(A) or 48(B) is open while the other valve is closed, and the controller 14 causes the valves 48(A) and 48(B) to reciprocate back and forth between open and closed depending upon which category of particle is currently being sorted.

The particle deflector 42 includes a pump 52, pressurized gas canister 54, a valve 56 and a nozzle 58. The pump 52 pumps gas into the gas canister 54 so that the gas canister 54 remains pressurized.

The valve 56 is in pneumatic communication with the gas canister 54 and in electrical communication with the controller 14. Upon receiving a triggering signal from the controller 14, the valve 56 opens and releases pressurized gas from the gas canister 54. In another embodiment, the valve 56 is a current-loop actuated (CLA) pulse wave valve such as a Pulsed Supersonic Valve C-211 by RM Jordan, Inc, Grass Valley, Calif. In yet another embodiment, the valve 56 is a piezo-electric valve or a solenoidal valve, which are known to those skilled in the art. Generally, the valve 56 is adapted to operate, open and close, up to approximately 500 times a second or more. Currently, the Pulsed Supersonic Valve C-211 can be operated to be open for pulse lengths as short as 20 microseconds. The scope of the present invention is intended to include any valve adapted to be electrically controlled.

The nozzle 58 is affixed to the valve 56 and gas released from the gas canister 54 flows through the nozzle 58 into the particle sorter 16(A). The nozzle 58 is aligned such that the released gas is directed towards the target zone 39 and such that the initial trajectory of the released gas is approximately perpendicular to the longitudinal axis 20 of the APSS 10.

At the appropriate time, the controller 14 sends a trigger signal to the valve 56 and the valves 48(A) and 48(B). Responsive to the trigger signal, the valve 48(A) opens and the valve 48(B) closes, thereby causing gas to flow through the particle receptor 40(A) and preventing gas from flowing through the particle receptor 40(B). The valve 56 opens responsive to receiving the trigger signal, thereby causing a burst of gas 62 to be released from the gas canister 54. The gas 62 deflects the trajectory of a target particle 60(A). The valves 48(A) and 48(B) remain in their current state until the particle 60(A) has entered the particle receptor 40(A), and then they reciprocate. In other words, if particle receptor 40(A) is a first particle receptor and particle receptor 40(B) is a second particle receptor, when target particle 60(A) is deflected toward first particle receptor 40(A), it is simultaneously deflected away from particle receptor 40(B). The controller 14 controls how long the valves 48 remain in a given state and how long the valve 56 remains open.

In some embodiments, particles are sorted by deflecting the trajectory of the particles using merely the valves 48(A) and 48(B). In this embodiment, when a particle of interest is in the target zone 39, the valve 48(A) is opened and the valve 48(B) is closed. The valves remain in that configuration until the particle of interest has been drawn into the particle receptor 40(A), and then, the valves reciprocate.

In some embodiments, the particles are sorted by the particle deflector 42 merely deflecting the trajectory of selected particles. In this embodiment, the particle sorter 16(A) does not include valves 48, or if the valves 48 are present, they remain open, and in either case, the pump 18 draws gas through the particle receptors 40(A) and 40(B) simultaneously. When a particle of interest is in the target zone 39, the controller 14 triggers the particle deflector 42, which then emits the burst of gas 62, thereby deflecting the particles of interest such that the particles of interest flow into the particle receptor 40(A).

Figure 4:
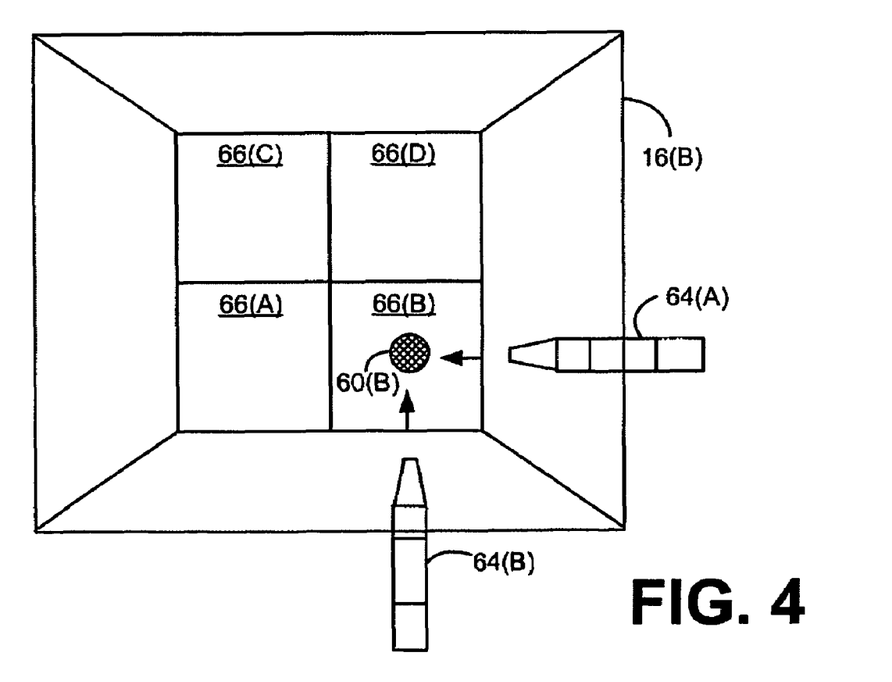
FIG. 4 is a block of a second embodiment of a particle sorter.

FIG. 4 depicts a top view of another embodiment of the particle sorter 16. The trajectory of a target particle 60(B) is into the page. The particle sorter 16(B) includes a plurality of particle deflectors 64 and multiple particle receptors 66. In this embodiment, the particle receptors 66(A), 66(C) and 66(D) are all for receiving particles whose trajectories have been deflected by at least one of the particle deflectors 64, and the particle receptor 66(B) is for receiving particles whose trajectories have not been deflected. The particle deflectors 64(A) and 64(B) are used to deflect particles towards the particle receptor 66(C). The particle deflector 64(A) is used singularly to deflect particles towards the particle receptor 66(A) and the particle receptor 64(B) is used to deflect particles towards the particle receptor 66 (D). As those skilled in the art will recognize, the particle sorter 16(B) can include more particle receptors 66 and more particle deflectors 64. In another embodiment, the particle deflectors are positioned in the particle sorter 16(B) at different longitudinal locations. In that case, the particle deflectors 64 that are longitudinally farthest from the particle receptors 66 deflect the particles that require the most amount of deflection, and the particle deflectors 64 that are longitudinally closest to the particle receptors 66 deflect the particles that require the least amount of deflection.

In some embodiments, the controller 14 controls not only how long the valve 56 of the particle deflector remains open, but also the escape velocity of the emitted gas 62. Such control of escape velocity is normally accomplished by controlling the pressure in the pressurized gas canister 54. Controlling the escape velocity provides a means for determining the amount of deflection that a given particle should receive. In this embodiment, the pump 52 is in electrical communication with the controller 14 such that the controller 14 can control the amount of pressure in the gas canister 54.

Figure 5:
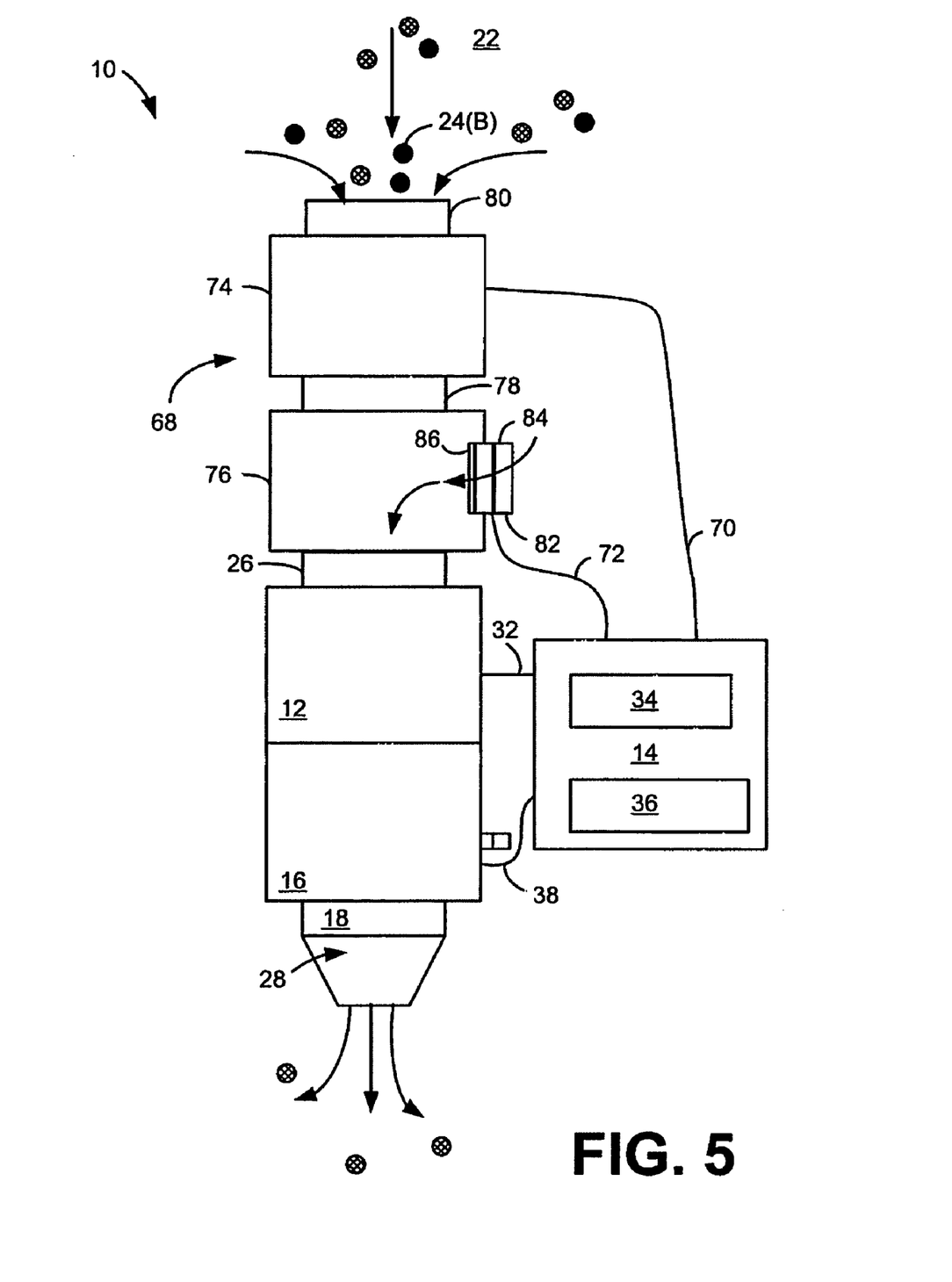
FIG. 5 is a block diagram of an embodiment of an aerosol particle sorter system (APSS) including a particle diluter assembly.

Referring to FIG. 5, in some embodiments, the APSS 10 includes a particle diluter assembly 68. The particle diluter assembly 68 attaches to the induction port 26 and is in electrical communication with the controller 14 via electrical connectors 70 and 72.

The particle diluter 68 includes a counter assembly 74 and a dilution chamber 76, which are in pneumatic communication via a connecting pipe 78. Particles 24 and gas 22 are drawn into the counter assembly via an induction port 80. The counter assembly 74 counts the particles 24 as they are drawn into the counter assembly 74 and communicates the particle count to the particle controller 14 via the electrical connection 70. From the counter assembly 74 the particles flow into the dilution chamber 76 via the connecting pipe 78 and through the induction port 26.

The dilution chamber 76 includes a dilution port 82 having a valve 84 and a filter 86 therein. If the particle current density in the particle sorter 16 is too great, then the particle sorter 16 can not effectively sort particles. To prevent this from happening, the controller 14 monitors the particle flux in the particle counter assembly 74, and when the particle flux reaches a predetermined level, the controller 14 opens the valve 84, thereby allowing gas to enter into the dilution chamber 76. The filter 86 is adapted to filter particles out of the gas flowing through the dilution port 82 such that clean gas dilutes the particle current density in the dilution chamber 76.

In some embodiments, the induction port 80 also includes a valve (not shown) which is in electrical communication with the controller 14. The controller 14 controls the particle current density in the APSS 10 by appropriately controlling the amount of gas and particles flowing through the induction port 80 and the amount of gas flowing through the dilution port 82.

In some embodiments, the pump 18 is a variable pump that is adapted to pump gasses at various rates, and the pump 18 is controllable by and in communication with the controller 14. The controller 14 uses the variable pump 18 to control the rate at which airborne particles flow through the APSS 10. By controlling the rate (velocity) at which gas and particles 24 are drawn into and through the APSS 10, the controller 14 controls the rate at which particles enter the target zone 39. Thus, the controller 14 can use the pump 18 to control the rate at which particles enter the target zone 39 of the particle sorter 16 such that the particle sorter 16 does not become swamped with more particles than it can handle. A variable pump can be used in conjunction with the particle diluter assembly 68 or independently thereof.

It should be emphasized that the above-described embodiments are merely possible examples of implementation. Many variations and modifications may be made to the above-described embodiments. All such modifications and variations are intended to be included herein within the scope of this disclosure and the present invention and protected by the following claims.

What is claimed is:

1. An apparatus for sorting particles entrained in a gaseous stream, the apparatus comprising:
   a pump operative to provide a gaseous stream and to entrain a particle in the gaseous stream;
   a particle scanner adapted to receive the gaseous stream and measure a characteristic of the particle entrained therein;
   a controller in electrical communication with the particle scanner, the controller adapted to classify the particle according to the measured characteristic of the particle, wherein the controller classifies the particle as belonging to one category of a plurality of categories;
   a first particle receptor positioned to receive a deflected particle such that, if the first particle is classified as belonging to the first category, the trajectory of the particle is generally deflected towards the first particle receptor;
   a second particle receptor positioned to receive a deflected particle such that, if the first particle is classified as belonging to the first category the trajectory of the particle is generally deflected away from the second particle receptor while being generally deflected toward the first particle receptor;

a sorter in pneumatic communication with the particle scanner and electrical communication with the controller, the sorter having an electrically controlled valve, wherein responsive to the particle being classified as belonging to a first category of a plurality of categories, the controller signals the valve to deflect the trajectory of the particle;

a first particle receptor valve positioned to provide access to the first particle receptor; and a second particle receptor valve positioned to provide access to the second particle receptor;

wherein the first particle receptor valve opens to enable the first particle receptor to receive particles and the second particle receptor valve opens to enable the second particle receptor to receive particles in response to a signal from a valve controller.

2. The apparatus of claim 1, wherein responsiveness to at least partially opening the electronically controlled sorter valve, a stream of gas is released from the valve, and at least a portion of the stream of gas alters the trajectory of the particle.

3. The apparatus of claim 1 wherein the electrically controlled valve is a piezo-electric valve.

4. The apparatus of claim 1 wherein the electrically controlled valve is a current-loop-amplitude valve.

5. The apparatus of claim 1, wherein, when the first particle receptor valve opens to provide access to an interior of the first particle receptor, the second particle receptor valve is closed such that a particle is prevented from entering the second particle receptor.

6. The apparatus of claim 1, wherein, with respect to the gaseous stream, the pump is positioned downstream of the particle scanner such that the gaseous stream is drawn past the particle scanner and toward the pump.

7. An apparatus for sorting particles entrained in a gaseous stream, the apparatus comprising:

pump means for providing a gaseous stream such that the gaseous stream entrains a particle;

scanning means for measuring a characteristic of the particle entrained;

controller means for classifying the particle according to the measured characteristic of the particle, the controller means in electrical communication with the scanning means, wherein the controller means classifies the particle as belonging to one category of a plurality of categories; and sorter means in pneumatic communication with the scanning means and electrical communication with the controller means, the sorter means having an electrically controlled atmospheric disturbance means for deflecting the trajectory of the particle, wherein responsive to the particle being classified as belonging to a first category of a plurality of categories, the controller means signals the atmospheric disturbance means to deflect the trajectory of the particle;

wherein the atmospheric disturbance means comprises:

a first valve, wherein responsive to the first valve being partially opened, the trajectory of the particle is generally deflected towards the first valve; and a second valve, wherein responsive to the second valve being partially closed, the trajectory of the particle is generally deflected away from the second valve.

8. The apparatus of claim 7, wherein the first valve and the second valve are each piezo-electric valves.

9. The apparatus of claim 7, wherein the first valve and the second valve are each current loop amplitude valves.

10. The apparatus of claim 7, wherein, with respect to the gaseous stream, the pump means is positioned downstream of the scanning means such that the gaseous stream is drawn past the scanning means and toward the pump means.

11. The apparatus of claim 7, further comprising:

first particle receptor means for receiving a deflected particle such that, if the first particle is classified as belonging to the first category, the trajectory of the particle is generally deflected towards the first particle receptor means.

12. The apparatus of claim 7, further comprising:

second particle receptor means for receiving a deflected particle such that, if the first particle is classified as belonging to the first category, the trajectory of the particle is generally deflected away from the second particle receptor means while being generally deflected toward the first particle receptor means.

* * * * *